United States Patent [19]

Schmitt et al.

[11] 3,982,543

[45] Sept. 28, 1976

[54] REDUCING CAPILLARITY OF POLYGLYCOLIC ACID SUTURES

[75] Inventors: Edward Emil Schmitt; Martin Epstein, both of Norwalk, Conn.

[73] Assignee: American Cyanamid Company, Stamford, Conn.

[22] Filed: July 16, 1974

[21] Appl. No.: 489,004

Related U.S. Application Data

[60] Division of Ser. No. 354,043, April 24, 1973, Pat. No. 3,867,190, which is a continuation-in-part of Ser. No. 190,290, Oct. 18, 1971, Pat. No. 3,736,646.

[52] U.S. Cl.............................. 128/335.5; 427/2; 428/394
[51] Int. Cl.$^2$.......................................... A61L 17/00
[58] Field of Search............ 128/335.5, 334 R, 339; 260/78.3; 117/138.8 A; 427/2; 428/378, 394

[56] References Cited
UNITED STATES PATENTS

| | | | |
|---|---|---|---|
| 2,668,162 | 2/1954 | Lowe | 260/78.3 |
| 3,297,033 | 1/1967 | Schmitt et al | 128/335.5 |
| 3,636,956 | 1/1972 | Schneider | 128/335.5 |

*Primary Examiner*—Dalton L. Truluck
*Attorney, Agent, or Firm*—Samuel Branch Walker

[57] ABSTRACT

Useful surgical elements consist of a sterile synthetic copolymer containing, by mole percent, about 15 to 85 percent glycolic acid and 85 to 15 percent lactic acid, which has enhanced tissue absorption as compared with polylactic acid and enhanced solubility in organic solvents as compared with polyglycolic acid and hence can be cast into sheets during preparation and implantation. Such surgical element may be used alone or in combination with polyglycolic acid or a coating for polyglycolic acid surgical elements. Other comonomers may be introduced into the system.

4 Claims, No Drawings

REDUCING CAPILLARITY OF POLYGLYCOLIC ACID SUTURES

CROSS-REFERENCES

This is a division of our application Ser. No. 354,043, filed Apr. 24, 1973, now U.S. Pat. No. 3,867,190, Feb. 18, 1975, which is a continuation-in-part of our then copending application Ser. No. 190,290, filed Oct. 18, 1971, now U.S. Pat. No. 3,736,646, June 5, 1973.

PRIOR ART

U.S. Pat. No. 2,683,136, Higgins, July 6, 1954, COPOLYMERS OF HYDROXYACETIC ACID WITH OTHER ALCOHOL ACIDS, discloses polymers of glycolic acid, there called hydroxyacetic acid, with other alcohol acids mentioning 10% lactic acid, 25 percent lactic acid, and 25 percent hydroxypivalic acid among others. These are disclosed as melt spinnable fibers.

U.S. Pat. No. 2,758,987, Salzberg, Aug. 14, 1956, OPTICALLY ACTIVE HOMOPOLYMERS CONTAINING BUT ONE ANTIPODAL SPECIES OF AN ALPHA-MONOHYDROXY MONOCARBOXYLIC ACID, discloses unique attributes of optically active precursors.

U.S. Pat. No. 3,297,033, Schmitt and Polistina, Jan. 10, 1967, SURGICAL SUTURES, discloses polyglycolic acid sutures and other surgical elements and their use in living mammalian tissue. Small quantities of other materials may be present in the chain, as for example, d,l-lactic acid, its optically active forms, homologs, and analogs. Said U.S. Pat. No. 3,297,033 incorporates a reference to U.S. Pat. No. 2,668,162 — Lowe, which quantifies a small amount of lactides as up to 15 percent, disclosing, for example, the preparation of a copolymer of 90/10 glycolide/lactide offers two advantages over the homopolymer of glycolide. One advantage is that the melting point of the copolymer is lower than the homopolymer, being in the neighborhood of 200°C; and the entire reaction can be conducted at approximately the melting point of the copolymer.

U.S. Pat. No. 3,463,158, Schmitt and Polistina, Aug. 26, 1969, POLYGLYCOLIC ACID PROSTHETIC DEVICES, has a number of pertinent definitions and discloses the use of bicomponent filaments in arterial prostheses. The use of both an absorbable and nonabsorbable component permit incorporation of permanent reinforcement in regenerating tissues which invades and replace the absorbable components.

U.S. Pat. No. 3,531,561, Sept. 29, 1970, Trehu, SUTURE PREPARATION, discloses preparation of a surgical suture from certain high molecular weight polylactides and mentions up to 15 percent comonomers which can be used in the production of copolymers.

Canadian Pat. No. 808,731, Fouty, Mar. 18, 1969, PREPARATION OF HIGH MOLECULAR WEIGHT POLYLACTIDES, also discloses certain copolymers.

Canadian Pat. No. 863,673, Schneider, Feb. 16, 1971, ABSORBABLE SUTURE, shows a surgical aid for joining or supporting living tissue such as a suture, film, tube, rod or mesh of a racemic or optically active polylactide containing as a comonomer up to about 15% of

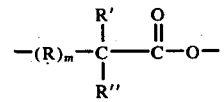

wherein R is lower alkylene, preferably methylene ($-CH_2-$) or ethylene ($-CH_2 CH_2-$), $m$ is 0 or 1, R' is hydrogen or lower alkyl, R'' is hydrogen or alkyl of up to about 22 carbons when $m$ is 0 and hydrogen or lower alkyl when $m$ is 1, and can be the same as R' or different. Illustrative of the comonomers" are "glycolide, β-propiolactone, tetramethylglycolide, β-butyrolactone, γ-butyrolactone, pivalolactone, and intermolecular cyclic esters of α-hydroxybutyric acid, α-hydroxyisobutyric acid, α-hydroxyvaleric acid, α-hydroxyisovaleric acid, α-hydroxycaproic acid, α-hydroxy-α-ethylbutyric acid, α-hydroxyisocaproic acid, α-hydroxy-β-methylvaleric acid, α-hydroxyheptanoic acid, α-hydroxyoctanoic acid, α-hydroxydecanoic acid, α-hydroxymyristic acid, α-hydroxystearic acid, and α-hydroxylignoceric acid."

U.S. Pat. No. 3,636,956, Schneider, Jan. 25, 1972, POLYLACTIDE SUTURES, with a series of filing dates, Oct. 19, 1962; Sept. 13, 1963; Apr. 20, 1965; Jan. 24, 1968, and May 13, 1970, and 79 claims discloses "lactide" polymers with claim 56 reciting up to 40 mole percent glycolic acid, implantation strength as sutures (Table VIII) up to 60 mole percent glycolide, and synthesis (Table VI) up to 70 percent glycolide. In each instance, the lactide is from a single antipodal species.

U.S. Pat. No. 3,620,218, Schmitt and Polistina, Nov. 16, 1971, CYLINDRICAL PROSTHETIC DEVICES OF POLYGLYCOLIC ACID, and a continuation-in-part thereof, Ser. No. 157,521, June 28, 1971, list a number of surgical uses of absorbable synthetic polymers. Such lists of uses are herein incorporated by this reference.

E. J. Frazza and E. E. Schmitt, "A New Absorbable Suture", J. Biomed. Mater. Res. Symposium, Vol. 1, pp. 43–58, John Wiley % Sons, Inc., New York, (1971) discloses information on the production and testing of polyglycolic acid sutures.

Several Technical Reports (6506, 6608) from the Walter Reed Army Medical Center report on polylactic acid sutures. A quarterly progress report, for the fourth quarter of 1970, AD 719264, gives data on solubilities of copolymers of glycolide/lactide.

British Patent 779,291, Kleine, 1957, PROCESS FOR THE PRODUCTION OF POLYESTERS OF HIGH MOLECULAR WEIGHT, discloses copolymers of glycolides and optically active lactides. Particularly interesting are disclosures on the differences of solubilities of the different optically active forms.

U.S. Pat. No. 2,363,511, Teeters, Nov. 14, 1944, MODIFIED GLYCOLIDE RESINS, discloses a process for the preparation of lactic acid modified polyglycolide resin by reacting lactic acid and glycolide acid at 200°C. for 2 hours at atmospheric pressure and one-half an hour under vacuum.

German Patent No. 1,153,902, Kleine, Sept. 5, 1963, OPTICALLY ACTIVE POLYESTERS, discloses a copolymer of optically active lactide with glycolide which is inactive. This patent shows that optically active lactic polymers have a shorter thermoplastic range and a high softening point, and are practically insoluble in acetone, benzene or dichloromethane at ambient temperatures.

Besides the above, surgical sutures and other surgical elements containing polymers of glycolic acid are described in:

U.S. Pat. No. 3,565,077 — Feb. 23, 1971, Glick, DENSIFIED ABSORBABLE POLYGLYCOLIC ACID SUTURE BRAID, AND METHOD FOR PREPARING SAME.

U.S. Pat. No. 3,620,218, Nov. 16, 1971, Schmitt and Polistina, CYLINDRICAL PROSTHETIC DEVICES OF POLYGLYCOLIC ACID.

U.S. Pat. No. 3,626,948, Dec. 14, 1971, Glick and McPherson, ABSORBABLE POLYGLYCOLIC ACID SUTURE OF ENHANCED IN-VIVO STRENGTH RETENTION.

U.S. Pat. No. 3,728,739, Apr. 24, 1973, Semp, STERILE SURGICAL GLOVES.

Reference is made to these patents which show additional prior art and for the definitions therein set forth.

Related data incorporated herein by this reference on manufacturing of polyglycolic acid, producing surgical elements thereof and its use for surgical purposes are disclosed in:

U.S. Pat. No. 3,414,939 — Dec. 10, 1968, Chirgwin, APPARATUS FOR QUENCHING MELT-SPUN FIBERS.

U.S. Pat. No. 3,422,181 — Jan. 14, 1969, Chirgwin, METHOD FOR HEAT SETTING OF STRETCH ORIENTED POLYGLYCOLIC ACID FILAMENT.

U.S. Pat. No. 3,435,008 — Mar. 25, 1969, Schmitt, Epstein and Polistina, METHOD FOR PREPARATION OF ISOMERICALLY PURE β-GLYCOLIDE AND POLYMERIZATION METHOD FOR GLYCOLIDE COMPOSITIONS EMPLOYING PARTIAL HYDROLYZATE OF SAID β-GLYCOLIDE.

U.S. Pat. No. 3,442,871 — May 6, 1969, Schmitt, Epstein and Polistina, PROCESS FOR POLYMERIZING A GLYCOLIDE.

U.S. Pat. No. 3,457,280 — July 22, 1969, Schmitt, Epstein and Polistina, α-GLYCOLIDE AND METHODS FOR THE ISOLATION THEREOF.

U.S. Pat. No. 3,468,853 — Sept. 23, 1969, Schmitt and Polistina, PROCESS OF POLYMERIZING A GLYCOLIDE.

U.S. Pat. No. 3,565,869 — Feb. 23, 1971, DeProspero, EXTRUDABLE AND STRETCHABLE POLYGLYCOLIC ACID AND PROCESS FOR PREPARING SAME.

U.S. Pat. No. 3,597,449, Aug. 3, 1971, DeProspero and Schmitt, STABLE GLYCOLIDE AND LACTIDE COMPOSITIONS.

U.S. Pat. No. 3,597,450, Aug. 3, 1971, Schmitt, Polistina, Epstein and DeProspero, PREPARATION OF GLYCOLIDE POLYMERIZABLE INTO POLYGLYCOLIC ACID OF CONSISTENTLY HIGH MOLECULAR WEIGHT.

U.S. Pat. No. 3,600,223, Aug. 17, 1971, Glick and McCusker, PROCESS FOR CLEANING POLYGLYCOLIC ACID FILAMENTS USEFUL AS ABSORBABLE SURGICAL SUTURES.

U.S. Pat. No. 3,728,839, Apr. 24, 1973, Glick, STORAGE STABLE SURGICALLY ABSORBABLE POLYGLYCOLIC ACID PRODUCTS.

U.S. Ser. No. 118,974, Feb. 25, 1971, Ramsey and Delapp, PREPARATION OF POLYGLYCOLIC ACID IN FINELY DIVIDED FORM now U.S. Pat. No. 3,781,349, Dec. 25, 1973.

U.S. Ser. No. 157,521, June 28, 1971, Schmitt and Polistina, POLYGLYCOLIC ACID PROSTHETIC DEVICES now U.S. Pat. No. 3,739,773, June 19, 1973.

U.S. Ser. No. 171,320, Aug. 12, 1971, Schmitt and Bailey, POLYGLYCOLIC ACID IN SOLUTIONS now U.S. Pat. No. 3,737,440, June 5, 1973.

U.S. Ser. No. 176,291, Aug. 30, 1971, Glick and Chirgwin, DOPE-DYED POLYGLYCOLIC ACID SUTURES.

U.S. Ser. No. 277,537, Aug. 3, 1972, Glick and Chirgwin, GREEN POLYGLYCOLIC ACID SUTURES AND SURGICAL ELEMENTS.

Other United States and foreign patents disclose surgical elements in which biodegradability and absorption results from the hydrolytic attack of tissue components on glycolic acid ester linkages in the polymer composing such surgical elements.

U.S. Pat. No. 2,552,027, Bird and Rochow, May 8, 1951, CASTING GELATIN TABLETS, in Column 6, line 18 and following shows gelatin formulations for slow and uniform release of therapeutic agents from a carrier matrix.

West German Patent No. 2,051,580, based on U.S. Ser. No. 868,899 of Oct. 23, 1969, and U.S. Ser. No. 79,309 of Oct. 8, 1970, discloses sustained release drugs using a lactide/glycolide copolymer as a carrier matrix.

U.S. Pat. No. 1,254,031, Jan. 22, 1918, Davis, SUTURE AND METHOD OF MAKING IT, shows a braided collagen suture immersed in collagen or glue to cause close adhesion of the braid, to fill up the interstices and provide a smooth uniform coating.

U.S. Pat. No. 2,401,291, May 28, 1946, Smith, RACKET STRING, shows a nylon on nylon coating. Similar coated strings have been used as sutures.

SUMMARY OF THE INVENTION

It has now been found that surgical elements made from a copolymer containing 15 to 85 mole percent of glycolic acid with the remainder lactic acid, or optionally, with minor amounts of additional monomers, retain their strength in tissues for a period longer than polyglycolic acid alone and have an affinity for a much wider variety of organic solvents. As used herein, the term lactic acid includes d-lactic acid, l-lactic acid and mixtures thereof, unless clearly restricted by naming as a particular optical configuration. At least 15 mole percent of polyglycolic acid linkages interspersed in the copolymer chain form hydrolyzable links which, on implantation in living mammalian tissue, hydrolyze, break the chain into short fragments, and permit the body chemistry to attack and dispose of the comonomer even though a homopolymer of the comonomer would be highly resistant to attack on implantation.

The presence of the comonomer linkages with the polyglycolic acid linkages increases the solubility of the copolymer in medically accepted common organic solvents such as chloroform or xylene or toluene. Both xylene and toluene have been used as a tubing fluid for boilable sutures made from catgut, and, hence, are medically accepted as a storage medium, and minor residual quantities are acceptable in the finished product. Chloroform has been used as a solvent and anesthetic by the medical professions for years. The copolymers may be stored in the presence of xylene or toluene, or in an environment containing controlled proportions thereof, so that the material is softer and plasticized for surgical uses in which such plasticity is a desirable attribute. Such solvents function to soften the copolymer so that woven or braided or felted elements may be softened and cause adhesion at points of contact of the filaments, so that a more sponge like element is obtained with the degree of attack by the solvent permitting a controlled change in porosity from an almost impervious film to a highly pervious felt or knit. Such control permits the implantation or surface use to control hemorrhage and gives very desirable characteristics as a surface bandage.

Exotic solvents, such as the lower alkyl cyanoacrylates, particularly methyl cyanoacrylate, can be used to partially solubilize the copolymer and because methyl cyanoacrylate is itself absorbable, methyl cyanoacrylate may be used to soften and adhere a prosthetic device to the surface of the skin or to interior tissues to permit surgical reconstruction with all of the components of the surgical reconstruction being absorbable and removable by the living mammalian tissue during the healing process.

Other useful cyanoacrylates include ethylcyanoacrylate, various alkoxyalkyl cyanoacrylates, fluorinated alkyl cyanoacrylates both straight chain and branched such as trifluoroisopropyl cyanoacrylate, fluorinated alkoxyalkyl cyanoacrylates and mixtures thereof, including those listed above.

The greater solvent solubility of a copolymer of lactic acid and glycolic acid can be utilized in coating a suture of polyglycolic acid with a solvent solution of the copolymer. For instance, a 50:50 mol percent copolymer of lactic acid and glycolic acid is sufficient soluble in chloroform that a braided polyglycolic acid suture may be dipped in such solution and without the solvent deleteriously affecting the polyglycolic acid, the copolymer is carried into the braid, and minimizes capillarity and increases the stiffness of the braid. The concentration of the copolymer in the solvent and the number of dips used is adjusted to give the degree of capillarity resistance, and stiffness, which is desired for a particular surgical procedure.

The dip coating procedure is also extremely useful in vascular prostheses. For instance, an arterial graft, used to replace a section of an artery which is defective, may be braided of a mixture of polyglycolic acid filaments and non-absorbable filaments such as Dacron, as more fully set forth in U.S. Pat. No. 3,463,158 supra, and the capillarity of the finished prosthetic device controlled by dipping in a chloroform solution of a 50:50 mol percent copolymer of lactic acid and glycolic acid. In the past, it has been frequently customary to dip woven or braided prosthetic devices in the blood of the subject, and let the blood coagulate so that immediate permeability is minimal, but the prosthesis is readily permeated by living tissue as the growing tissue invades the graft. Using a dip coating in the copolymer permits adjustment of permeability more accurately, and prior to the time of use. It also permits control of the rate of absorption of the polyglycolic acid as the coating must be invaded before the polyglycolic acid filaments are subject to hydrolytic attack.

Similarly in heart valves, patches for abdominal defects, bone splice pins, inserted tubes and arteries, burn dressings, and protective sheets on the surface of the external skin or internal organs, the rate of hydrolytic attack by living mammalian tissue on polyglycolic acid may be modified by a coating of the copolymer which is solvent soluble and therefore readily applied without compromise or modification of the integrity of the surgical element of polyglycolic acid.

In some surgical procedures, as for example inserting a bone pin, it is convenient to have an outer protective coating so that the pin maintains its full size and strength for a greater length of time before it begins to be absorbed, and yet once the outer surface is penetrated and hydrolytic attack started, the rate of hydrolysis is increased by the more rapidly absorbability of polyglycolic acid as contrasted with the copolymer.

The control of the rate of absorption advantageously increases the scope of procedures available to the surgeon.

Definitions in the textile trades are frequently somewhat ambiguous. For purposes of the present document, certain terms are defined:

A "filament" is a single, long, thin flexible structure of a non-absorbable or absorbable material. It may be continuous or staple.

"Staple" is used to designate a group of shorter filaments which are usually twisted together to form a longer continuous thread.

An absorbable filament is one which is absorbed, that is digested or dissolved, in living mammalian tissue.

A "thread" is a plurality of filaments, either continuous or staple, twisted together.

A "strand" is a plurality of filaments or threads twisted, plaited, braided, or laid parallel to form a unit for further construction into a fabric, or used per se, or a monofilament of such size as to be woven or used independently.

A "fabric" is a three dimensional assembly of filaments, which may be woven, knitted, felted or otherwise formed into a flexible sheet having two layer dimensions and a thinner thickness dimension. A fabric may be cut to a desired size before or at the time of use.

Except where limited specifically or by context, the word fabric includes both absorbable and non-absorbable cloth, or a fabric or cloth that is partially of absorbable polyglycolic acid.

A "dressing" is a woven, knitted, felted or braided fabric, of at least one layer, which is designed to protect a wound and favor its healing. As used herein, the term dressing includes bandages, insofar as they contact the wound itself. The dressing may be entirely internal.

A "bandage" is strip of gauze, or other material used to hold a dressing in place, to apply pressure, to immobilize a part, to obliterate tissue cavities or to check hemorrhage. Except insofar as the bandage comes in contact with a wound, or the exudate from a wound, there is no need for the bandage to be of an absorbable polymer. If the bandage may be in a position where absorbability by living tissue of at least part of the bandage is desirable, at least that part should be of an absorbable material.

A "solid prosthetic device" is a thin solid sheet, or plate, or tube, which may be split, or bar, or nail, or screw, or pin or other solid shape which has inherent mechanical strength in compression, bending and shear to act as a solid discrete surgical reinforcing element, and has at least one dimension greater than 2 millimeters, and which may have a dimension as great as about 200 millimeters, or as required, to fit into or adjacent to and furnish mechanical support and reinforcement to a bone, or bones, or gland, or organ, for support during a healing process.

The size and shape of the prosthetic devices, or prostheses, is controlled by usage. For example, in the human body, in the case of a bone fracture, a pin is used to reinforce a bone, and is of such size as to be a tight driving fit into a central portion of the bone, or a hole drilled into a bone. Such a pin can be from about 1/16 inch diameter and 3/8 inch long for finger bones, or for children, up to 1 1/4 inch diameter and 6 inch length to reinforce the femur, or thigh bone of large adult humans, or even larger for valuable race-horses or other mammals.

The support may be in part directive of growth, as for example in nerve tissue, which grows slowly, and as a result has regeneration impaired by the more rapid growth of scar tissue which can block the growth of the nerve tissue. With a wrap-around sheath of PGA sheet, or PGA fabric or a split or solid tube used to support, place, hold and protect; regeneration of nerve tissue and function is greatly aided. Other factors may inhibit regeneration of nerve tissue or function, but with the exclusion of scar tissue, such other factors may be separately treated. Our copolymers are particularly useful in splicing nerves because the composition of the polymer can be adjusted to give a selected absorption rate, depending on the desires of the using surgeon.

For different purposes and in different types of tissue the rate of absorption may vary but in general an absorbable prosthesis should have as high a portion of its original strength as possible for at least three days, and depending on usage, strength may be desired for a much longer time. For instance, a bone reinforcing element may need strength for several months or more. A tendon reinforcement may need strength for even longer. The rate of absorption in tissues varies with the tissue, so a wide range of absorption rates is useful.

In common with many biological systems, the requirements are not absolute and the rate of absorption as well as the short-term strength requirement varies from patient to patient and at different locations within the body, as well as with the thickness of the section of the copolymer.

The copolymer may be formed as tubes or sheets for surgical repair and may also be spun as thin filaments and woven or felted to form absorbable sponges or absorbable gauze, or used in conjunction with other compressive structures as prosthetic devices within the body of a human or animal where it is desirable that the structure have short-term strength, but be absorbable. The useful embodiments include tubes, including branched tubes or Tees, for artery, vein or intestinal repair, nerve splicing, tendon splicing, sheets for tying up and supporting damaged kidney, liver and other intestinal organs, protecting damaged surface areas such as abrasions, particularly major abrasions, or areas where the skin and underlying tissues are damaged or surgically removed. A lung or other internal organs may find the copolymers useful.

In surgical techniques involving internal organs, hemorrhage may be a major problem. Some of the organs have such tissue characteristics that it is very difficult to use sutures or ligatures to prevent bleeding. For example, the human liver may suffer traumatic damage or exhibit tumors or for other reasons require surgery. In the past it has been very difficult to excise part of the liver or to suture the liver without the combined problems of the sutures cutting out and hemorrhage at the surface causing such major complications as to either prevent surgery or cause an unfavorable prognosis.

It is now found that a sponge or pad or velour of our copolymers may be used to protect the surface and permit new feats of surgical intervention. For instance copolymer filaments may be formed into a woven gauze or felted sponge of a velour; preferably the construction is fairly tight by textile standards and such sponge may be placed on the surface of the bleeding organ such as the liver or a lung with either gentle suturing to hold the element or with ties in the nature of ligatures to hold the element in position with a certain amount of body fluids flowing into the sponge and being absorbed, which results in hemostasis and prevention of further loss of body fluids. If a liver or lung is so repaired, the organ may be replaced in the body cavity and the wound closed. The absorbable copolymer elements usually maintain a substantial portion of their strength for at least 7 days which permits healing processes to occur in many tissues. If a high ratio of lactic acid is used in the copolymer, absorption may be delayed for many months, in part depending on the blood supply to the site of the prosthesis.

Pads, bandages or sponges of the absorbable copolymer are extremely useful in surgical techniques in which it is the intent to remove the major portion or all of such sponges, felt or pad but through inadvertence or accident part of it may remain. For instance in a surgical operation, one of the problems which arises is the lint from cotton sponges remaining in the wound. If copolymer sponges are used, any small fragments which are accidently displaced are absorbed without incident and even if a sponge is left in the wound, the deleterious effects are minimal. It is not desired that large volumes filled with sponges, particularly if the sponges are or become saturated with blood, remain in body cavities. The absorption of the blood clot appears to present more of a problem than the copolymer. The location is also critical as some locations are more sensitive to blood clots than others. Small sponges result in minimal side effects.

The use of the copolymer as a sponge or pad is particularly advantageous for surface abrasions. In the past it has been necessary to put on a dressing and avoid having the non-absorbable dressing grow into the tissue at all costs. Because the copolymer absorbs, if elements of the gauze are beneath the regenerating tissue level, the tissue will regenerate and absorb the copolymer with the residual copolymer in the scab falling off when the scab is displaced.

In surgery various tissues need to be retained in position during healing. Defects and wounds of the abdominal wall, chest wall and other such tissues need to be reconstructed. For a hernia, a permanent splice or reinforcement is often desired. For some surgical procedures, a temporary reinforcing is desired to provide strength while body tissues are healing; and after the body tissues have assumed the load, foreign components are no longer desired. Tissue retention is readily accomplished using either an absorbable monofilament or polyfilament fabric or mesh or by using a non-absorbable material such as polyethylene or polypropylene or polyester woven as a bicomponent mesh or knit with the absorbable copolymer. The use of a bicomponent fabric has the advantage of giving additional early strength for holding the tissues in position during initial regeneration with the copolymer portions being absorbed, and permitting body tissues to invade and reinforce the permanent mesh. A copolymer is selected which has the absorption rate desired for the surgical procedure.

In common with other surgical procedures, it is often desirable that a bicomponent structure be used which provides the spacing desired for non-absorbable elements, with the absorbable element holding the structure in a desired geometrical configuration at the start of the healing process. As the copolymer element is absorbed, regenerated tissue invades, so that the non-absorbed element is left in a desired configuration, interlaced with living tissue in a stress-transferring relationship.

The choice of a non-absorbable reinforcement, a partially absorbable reinforcement, or a completely absorbable reinforcement is a matter of surgical judgment, based upon the condition of the patient, the body structure under treatment, and other medical factors. The present copolymer fabric, or bicomponent fabrics using the copolymer for the absorbable portion or different copolymers for different absorption rates greatly expands the scope of reinforcement available to a surgeon, and permits using absorbable structures for reinforcement in many new medical techniques.

Certain uses of bicompoment fibers are set out in U.S. Pat. No. 3,463,158 supra. The greater range of rates of absorption permitted by using the present copolymer systems for the absorbable element or elements extends the range of absorption rates and permits using two or more components, with controllable absorption rates for each.

The copolymer may be exposed to moisture during storage before use, or may be of a lower molecular weight, both of which increase the rate of absorption by the body tissues, so that the surgical sponge in an extraction, or the prosthetic implant, has a controllable rate of absorption.

The medical uses of the present copolymers include, but are not necessarily limited to:

A. The Copolymer Itself
  1. Solid Products, molded or machined
     a. Orthopedic pins, clamps, screws and plates
     b. Clips (e.g., for vena cava)
     c. Staples
     d. Hooks, buttons and snaps
     Bone substitutes (e.g., mandible prosthesis)
     e. Bone substitutes (e.g., mandible prosthesis)
     f. Needles
     g. Non-permanent intrauterine devices (spermocide)
     h. Temporary draining or testing tubes or capillaries
     i. Surgical instruments
     j. Vascular implants or supports
     k. Vertebral discs
     l. Extracorporeal tubing for kidney and heart-lung machines
  2. Fibrillar Products, knitted or woven, including velours
     a. Burn dressings
     b. Hernia patches
     c. Absorbent paper or swabs
     d. Medicated dressings
     e. Facial substitutes
     f. Gauze, fabric, sheet, felt or sponge for hemostasis, as for example of the liver or other internal organs
     g. Gauze bandages
     h. Dental packs
     i. Surgical sutures
  3. Miscellaneous
     a. Flake or powder for burns or abrasions
     b. Foam as absorbable prosthesis
     c. Substitute for wire in fixations
     d. Film spray for prosthetic devices
B. In Combinations
  1. Solid Products, molded or machined
     a. Slowly digestible ion-exchange resin
     b. Slowly digestible drug release device (pill, pellet)
     c. Reinforced bone pins, needles, etc.
  2. Fibrillar Products
     a. Arterial graft or substitutes
     b. Bandages for skin surfaces
     c. Burn dressings (in combination with other polymeric films.)

The synthetic character and hence predictable formability and consistency in characteristics obtainable from a controlled process are highly desirable.

The copolymers of glycolic acid with lactic acid and/or the other monomers herein mentioned have lower melting points. Polyglycolic acid has a crystalline melting point of about 230°C. which is not far below the "ceiling temperature" at which the polymer tends to degrade, and the molecular weight becomes lower. The present copolymers, depending upon the other monomer or monomers present, and the percentages thereof have melting points which may be as low as about 150°C. and have a greater temperature range between the crystalline melting point and the ceiling temperature. This permits heating the copolymer until it attains greater fluidity, and hence is more easily melt spun or cast or otherwise formed. The copolymers give different degrees of crystallinity dependent upon the comonomer, and the ease with which the molecules slide past each other under physical stress. The copolymers normally have greater ductility and a higher impact strength and higher shear strength in proportion to the tensile strength, which permits more readily forming the materials.

Melt spinning and drawing usually results in greater tensile strength with a trade-off in lower ductility and lower impact strength.

For fibrous products in the smaller sizes, the high tensile strength, or tenacity is highly advantageous. For solid devices such as bone pins or clips, staples and other forms of retaining members, a higher ductility and higher impact strength becomes relatively more important. The present copolymers permiting a wider choice of such characteristics by changes in the ratios of the monomers.

The most convenient method of sterilizing the present copolymers is by heat under such conditions that any microorganisms of deleterious materials are rendered inactive. A second common method is to sterilize using a gaseous sterilizing agent such as ethylene oxide. Other methods of sterilizing include radiation by X-rays, gamma rays, neutrons, electrons, etc., or high intensity ultrasonic vibrational energy or combinations of these methods. The present materials have such physical characteristics that they may be sterilized by any of these methods.

Different sterilizing procedures may be required, when the present copolymers are used as a repository for therapeutic agents.

One of the early repositories meeting considerable acceptance was bees wax for certain of the penicillins. The penicillin was suspended in the bees wax, the mixture injected into a patient, and the penicillin thus released from the repository over a period of several days or longer. After the penicillin had been released, the bees wax remained in the subject as an unesired foreign body for an extended period of time.

The present copolymers permit similar usage as a repository except that after the drug is released, the copolymer itself dissolves and leaves nothing as an undesired residue in the tissue.

Controlled release rates are very desirable. Some drugs are injected with the intention that the faster the drug is absorbed, the better. Others need to be emplaced under such conditions that the maximum concentration released is within desired limits, and yet the drug is made available over an extended period of time so that a single implantation can last for whatever length of time is desired for a particular medical procedure. For instance as a birth control pill, the blood levels of certain steroids are to be maintained at a low level for prolonged periods. The steroid may be dissolved in chloroform, and the present copolymers additionally dissolved in the chloroform and the mixture cast to form a film. By using copolymers which contain from 85 percent glycolic acid down to 15 percent glycolic acid, the relative rates of release and absorption can be varied widely, with these steroids.

For contraceptive purposes, an effective storage bank may be desired with a release time of several years. The medicament containing absorbable polymer may be shaped and used as an intrauterine contraceptive device, having the advantages of both shape and the released medicament, and additionally an inherently limited effective life. With other steroids used for the treatment of pathological conditions, the choice may be that the entire dosage is released uniformly over a period of from 1 to 30 days, or so. For other drugs the release period desired may be even more widely variable. For some antibiotics an effective concentration for 1 or 2 days is preferred for control of some pathogens.

Alternatively the absorbable copolymers may be ground and mixed with the drugs as fed to a tabletting press, or the mixture may be moistened with a binding liquid and compressed. For instance an absorbable copolymer may be mixed with steroids, and compressed either dry or with a small amount of chloroform to give binding characteristics. The pellet is compressed to the size and shape desired for a particular implantation.

Additionally such cast or compressed drug release forms may be used orally. The absorbable copolymers in general have a relatively slow hydrolysis rate in the acid environment in the stomach but a much higher hydrolysis rate in the more alkaline environment of the intestine, particularly under the influence of esterases present in the normal intestine. For oral administration, the copolymers permit flexibility in release rates. For oral ingestion, any effective release must be achieved before the elimination of the residual copolymer, which in humans is normally within 48 hours. The time in other mammals may vary.

For implantation in tissues, either subcutaneously, intramuscularly, or in other areas, a copolymer is used which gives the desired release rate and then after its therapeutic effect is achieved, the residual absorbable copolymer is absorbed which frees the tissues from foreign bodies.

Whereas the repository as a sheet or pellet may be introduced beneath the skin, a convenient form is to shape the absorbable copolymer-medicament mixture as a thread, which is implantable beneath the skin as readily as a suture, and which can be implanted at a cosmetically convenient location for systemic medicaments, or in a selected area, for medicaments whose application is to be localized.

Additional materials such as silicones may be coated upon the copolymer repository where it is desired that the release rate be further delayed. For instance there are pathological conditions under which the release of a drug or hormone may be desired for the remaining life of a subject. In fact the remaining life of a subject may be determined by an effective release of a drug from an implanted repository, or other source.

Sterility is essential in the subcutaneous implants, and desirable in oral forms. The absorbable copolymer itself may be sterilized as indicated above for surgical elements including sutures. If the medicament is adaptable to radiation, heat, or ethylene oxide sterilizing cycles, such may be used. For more labile medicaments, the absorbable repository forms are made using sterile techniques from sterile components, or a sterilization procedure is chosen which is compatible with the medicament characteristics.

In the following examples, and claims, all parts and percentages are by weight, unless otherwise specified.

EXAMPLE 1

Preparation of Inactive Lactide

Into a 100 millimeter distilling flask was introduced 750 grams of commercial 85% lactic acid [$(\alpha_D)^{25}$ = +.072, C=4.0 g./100 ml.] and the water distilled off with the temperature increasing to 150°C. The pressure was reduced to 20 millimeters of mercury and the acid distilled followed by further heating to 230°–250°C. which decomposed the polylactic acid to form the dimer which was distilled and collected. The distilled lactide was recrystallized from ethyl acetate to yield an optically inactive lactide with a melting point of 120°–123°C. (U.S. Pat. No. 2,703,316 reports m.p. 124°–125°C.).

EXAMPLE 2

Preparation of Optically Active Lactide

A 1 liter, three-necked flask was charged with 450 grams of crystalline L(+) commercial lactic acid [$(\alpha_D)^{25}$ = +1.42, C=20 g./100 ml.] The charge was heated to remove water with pressure being reduced to 10 millimeters of mercury and distillation conducted at 230°–270°C. The distillate was recrystallized from isopropanol to yield 38 grams of an optically active lactide with a melting point of 90° to 95°C. and an optical rotation in benzene $(\alpha_D)^{24}$ = −288.3, C=1.17 g./100 ml.

EXAMPLE 3

Preparation of Polylactide

A heavy wall test tube was charged with 3 grams of lactide and 0.3 percent of litharge based on the weight of lactide. The reaction tube was evacuated and sealed. The tube was heated at 145°–150°C. for 31 hours and allowed to cool at room temperature. Using the lactide from Example 2, a clear poly-L-lactide acid was obtained which had an optical rotation of $(\alpha_D)^{24}$ = −168.8, C=1.0 g./100 ml., in benzene.

Other useful catalyst systems are described in the patents referred to above. Note for example $SnCl_2 \cdot 2H_2O$, stannous chloride dihydrate, such as described in U.S. Pat. No. 3,442,871, Schmitt, Epstein and Polistina, May 6, 1969, PROCESS FOR POLYMERIZING A GLYCOLIDE, which also describes the use of chain terminating agents such as lauryl alcohol. The present invention is not limited to any particular polymerization catalyst, or system of polymerization.

EXAMPLE 4

A series of polymers were produced using the method of Example 3 and the resultant product tested by nuclear magnetic resonance to establish the ratio of lactic acid units to glycolic acid units in the copolymer. The following results were obtained;

| Ratio by Weight lactide/glycolide | Mole % Lactide | Found by NMR Mole % Lactide | Found by NMR Mole % Glycolide |
|---|---|---|---|
| 100/0 | 100 | 100 | 0 |
| 99.6/.4 | 99.4 | 100 | 0 |
| 99/1 | 98.7 | 96 | 4 |
| 97/3 | 96.3 | 95 | 5 |
| 95/5 | 94.2 | 92 | 8 |

These results confirm that a true copolymer is obtained, and not a mixture of homopolymers.

EXAMPLE 5

Polymers were prepared as in Example 3 containing 75 percent lactic 25 percent glycolide and 50 percent lactic 50 percent glycolide. The 75/25 polymer was decomposed on implantation in 40 days with a thin ghost formation. After 90 days, a thin fiber scar remained. The tests showed that the higher glycolide concentration results in more rapid absorption. The 50/50 polymer absorbed similarly, but appeared to absorb more rapidly.

EXAMPLE 6

Cyclic Comonomers with Glycolide

A group of samples were prepared using the procedure of Example 3, with cyclic comonomers using glycolide as the major component. These were tested in rabbits, with the following results:

Table I

| Copolymerization of Glycolide with Cyclic Monomers | | |
|---|---|---|
| Comonomer | Weight % Comonomer | Absorption Time |
| γ-Butyrolactone | 15 | 30–60 days |
| γ-Caprolactone | 15 | 15–30 days |
| ε-Caprolactone | 15 | 15–40 days |
| Ethylene Carbonate | 15 | 30–60 days |
| Ethylene Carbonate | 25 | 15–30 days |
| Keto-1,4-dioxane | 10 | 15–30 days |
| Pivalolactone | 5 | 30–60 days |
| Propylene Carbonate | 15 | 15–30 days |
| 2,2,4-Trimethyl-3-hydroxy-3-pentenoic acid β lactone | 5 | 15–26 days |
| γ-Valerolactone | 15 | 15–20 days |

Other useful comonomers include β-propiolactone, tetramethylglycolide, β-butyrolactone, and intermolecular cyclic esters of α-hydroxybutyric acid, α-hydroxyisobutyric acid, α-hydroxyvaleric acid, α-hydroxyisovaleric acid, α-hydroxycaproic acid, α-hydroxy-α-ethylbutyric acid, α-hydroxyisocaproic acid, α-hydroxy-β-methylvaleric acid, α-hydroxyheptanoic acid, α-hydroxyoctanoic acid, α-hydroxydecanoic acid, α-hydroxymyristic acid, α-hydroxystearic acid, α-hydroxylignoceric acid, α,α-diethylpropiolactone, trimethylene carbonate, 2,5-diketomorpholine, ethylene oxalate and phthalide.

Absorbability of polymeric materials is conveniently tested by implanting a strip approximately 3 inches long in experimental rabbits between the panniculus carnosis and deeper abdominal musculature through a bluntly dissected tunnel running from one side of the mid-line to the other in each of four rabbits using strict aseptic surgically acceptable techniques. Four rabbits are implanted with two being sacrificed after 45 days and the other two at 90 days. If the material does not show evidence of absorption by 90 days, the material is absorbed too slowly to be useful in absorbable surgical elements. After absorbability in tissue is established, tests of utility for various surgical elements may be made.

For instance sutures made from synthetic polymeric materials are conveniently implanted under the skin of the abdomen of test rabbits, and after 7 and 15 days dissected out of the rabbit and tested for remaining strength. For sutures, it is desirable that a high proportion of strength be retained for at least 7 and better 15 days, and that the material be rapidly absorbed thereafter. For other surgical uses, the desired rate of absorption varies considerably. In a repository, absorption times of from two days to several years are useful. For bone pins and other elements, absorption times of several months are frequently useful.

The metabolism of mammalian tissue absorbable polymers can be considered to occur in two steps:
a. Breakdown of the large insoluble polymeric molecule to smaller soluble units.
b. Removal of the smaller soluble units from the site and eventually from the body.

For polymers containing polyglycolide linkages, step (a) occurs by hydrolysis, or reaction with the water in the body fluids in tissue without the necessity of enzyme participation. It is believed that the hydrolysis reaction converts the polyglycolide linkages to glycolic acid.

Radioactive tracer experiments show that part of the glycolic acid is excreted as carbon dioxide in expired air. This indicates that enzymatic catalysis is involved in step (b). When radioactive glycolic acid itself is injected into rats, the excretion products are similar.

The mechanism by which an absorbable material is broken down in tissue is less important, with respect to tissue irritation, than the actual nature of the intermediate or ultimate metabolites. Catgut for instance is irritating because its proteinaceous byproducts cause toxic reactions, not because enzymatic proteolysis is occurring. Similarly, polyglycolic acid shows little tissue irritation because non-toxic breakdown products are formed.

If the monomers copolymerized with the glycolic acid cause no tissue irritation, the breakdown products are innocuous. A comonomer is chosen whose toxicity is acceptable for a specific usage. Lactic acid is well known as a body metabolite.

Because the copolymers are absorbed by a hydrolytic action, the copolymers tend to hydrolyze on storage if moisture is present. For prolonged storage, the surgical elements are best kept in a bone dry atmosphere—less than about 50 water parts per million of ambient air. An adequate storage life of months or even a few years may be achieved with a higher moisture environment.

Absorbable Medullary Rod

Longitudinal incisions were made on the superior surface of the hind legs of anesthetized rabbits to expose the upper end of the femur, close to the point of attachment to the hip. At a point about 1 inch from the neck portion, the shaft of the femur was cut completely through by means of a small circular saw attached to an air drill. A hole about one-eighth inch in diameter was drilled through the bony process known as the greater trochanter vertically into the narrow cavity of the shaft portion of the femur. The cut ends of the femur shaft were approximated and while they were held firmly in place a medullary rod of an absorbable copolymer about two inches in length and about one-eighth inch in diameter was driven through the hole in the trochanter into the narrow cavity past the point at which the shaft of the femur had been parted. The effect of the medullary rod was to hold the cut ends of the femur shaft firmly in place. The top end of the medullary pin was flush with the surface of the trochanter.

The parted soft tissues were approximated with sutures, the injured legs were splinted with wooden tongue depressors affixed to the leg with adhesive tape and the animals were returned to their cages. X-rays were taken of the injured legs at weekly intervals and the progress of new bone formation was observed. Animals were sacrificed at the end of 6, 12, 18 and 24 weeks and the femurs which had been operated upon were dissected out and examined. Copolymers having an absorption time of several months are useful in strengthening major body bones.

Premolded plates, pins, nails, screws, clips, surgical needles, hypodermic needles, heart valves, valve retaining sleeves, or cushions, and the like can be made from these copolymers. For instance a very slowly absorbing copolymer can be used as an implant for a cartilage replacement, which absorbs at such a rate as to minimize foreign body reactions, and yet has a usefully long reinforcing life. More rapidly absorbing copolymers are preferred for gauze, bandages, or temporary protection on the surfaces of the external skin, or internal organs, which surgical elements would be designed to be absorbed more rapidly, after completing their assigned task. For some such usages a dye or pigment or an antibiotic may be incorporated in the implant.

Some such uses are described and illustrated in U.S. Pat. No. 3,463,158 supra, which disclosure of uses for absorbable elements is herewith herein incorporated by this reference.

EXAMPLE 7

Using the procedure of Example 3, polymers were prepared containing L-lactide with various proportions of glycolide. As the cyclic rings of the glycolide and L-lactide are opened during polymerization, the chain in the polymer that results contains the linkages from L-lactide and glycolide. The product may be spoken of as L-lactic acid glycolic acid copolymers without reference to whether it was made from polymers of lactic acid and glycolic acid or the lactic and glycolic acid in monomeric form.

Samples were prepared containing

| Sample | | |
|---|---|---|
| No. 1 | 95% L-lactide | 5% Glycolide |
| No. 2 | 90% L-lactide | 10% Glycolide |
| No. 3 | 85% L-lactide | 15% Glycolide |
| No. 4 | 80% L-lactide | 20% Glycolide |

At the time of implant, all materials had excellent handling properties. They were strong, quite pliable, and not brittle. After exposure for 3 hours to 3 days to air, and ambient moisture, they became opaque.

Samples of these polymers were inserted under the skin of test rabbits and remained for 45 or 90 days. The rabbit was sacrificed, and the tissue examined. Gross examination showed after 45 days:

No. 1 — The copolymer strip was cracked, flakey, and bunched together in one area. It appeared to be virtually undigested.

No. 2 — This strip was more "mushy" than No. 1, but was also knotted up in one area. There was evidence of some digestion.

No. 3 — The results appeared essentially the same as Strip No. 2.

No. 4. — The results appeared essentially the same as Strip No. 2.

After 90 days on gross examination, the results were:

No. 1 — There was a heavy fibrotic capsule or tract. There were flakes of the original copolymer strip discernible. Partial digestion had taken place.

No. 2 — As No. 1 but seemingly there was more digestion.

No. 3 — The results appeared essentially the same as in No. 2.

No. 4. — The results appeared essentially the same as in No. 2.

On microscopic examination, the microscopist reported that after 45 days:

No. 1 — The copolymer strip was pretty much intact, although somewhat cracked. Viewed in cross-section, the material has split into lengthwise segments. There was a fairly definite capsule composed of fibroblasts, fibrocytes and fibroconnective tissue. There was no tissue ingrowth between the split segments. Cellular reaction was very minimal, No. 2 — This copolymer looked totally different than No. 1 in that it was very granular in appearance. It was also split into longitudinal segments. There was a definite capsule with an unilateral accumulation of polymorphs. There was, however, some tissue ingrowth between individual segments. There was evidence of active digestion. Not more than 1–3 percent of copolymer had been absorbed, No. 3 — The copolymer sample looked much like No. 2 but was not segmented into distinct pieces. Rather, it was disintegrated into granular clumps. There was much tissue ingrowth. Digestion was estimated at 1–3 percent, No. 4 — The only difference between No. 4 and No. 3 was that No. 4 was more disintegrated.

After 90 days:

No. 1 — The copolymer was beginning to assume the granular appearance of Nos. 2–4 at 45 days. The strip was very cracked and segmented, the segments being randomly dispersed. Each segment was encapsulated by fibroconnective tissue and foreign body giant cells. Still, however, the edges were quite sharply delineated in many places. The overall cellular response to No. 1 at 90 days was more reactive than at 45 days. About 5 percent digestion had occurred.

No. 2 — The cellular pattern was very similar to that of No. 1, but there were more foreign body giant cells. The outlines of the copolymer were very indefinite; frequently the copolymer and foreign body giant cells merged. The foreign body giant cells assumed the elongate shape of the copolymer segments. Each section was completely encapsulated. Digestion was estimated at 10–20 percent.

No. 3 — The cellular pattern of No. 3 was much like No. 2. A few sections were totally digested. Digestion was estimated at 15–30 percent.

No. 4 — The cellular response to No. 4 was similar to that of Nos. 2 and 3. About 20–30 percent digestion had taken place.

This histologic data indicate that there is a direct correlation between the amount of glycolide in the copolymer and the rate of absorption; that is, the greater the percentage of glycolide, the faster the rate of absorption.

Tissue reaction was normal throughout the entire test period.

EXAMPLE 8

Similar tests were run using 75 percent L-lactide and 25 percent glycolide as well as 50 percent lactide and 50 percent glycolide. The polymer appeared absorbed after about 40 days.

In summary, the results were:

Table II

| Polylactic Acid Containing Glycolic Acid Units | | | |
|---|---|---|---|
| Monomer | Wt-% Comonomer | Wt-% | Absorption |
| L-lactide | 95 | Glycolide | 5 | 90 days-5% digested |
| L-lactide | 90 | Glycolide | 10 | 90 days-10–20% digested |
| L-lactide | 85 | Glycolide | 15 | 90 days-15–30% digested |
| L-lactide | 80 | Glycolide | 20 | 90 days-20–50% digested |
| L-lactide | 75 | Glycolide | 25 | 40 days |
| L-lactide | 50 | Glycolide | 50 | 40 days |

Because of the variations in polymerization, conditions for the treatment of polymer, such as exposure to moisture before implantation, storage time, and because of differences in the sizes of the strips, or filament implanted, results between different laboratories and different workers vary — but in general, it appears that the higher the concentration of the glycolic acid component, the more rapid the tissue absorption and the less interaction with the tissues. Because the higher concentration of lactic acid in the polymers increases solubility in the common organic solvents such as benzene, toluene and the xylenes as well as in the less common solvents such as phenol, cresol, acetone, chloroform, ethy acetate, anisole, methylene chloride, dimethyl formamide, and acetic acid, those uses in which solvent solutions are desirable, a copolymer in the range of 15 to 85% glycolic acid linkage by weight optimizes the advantages of solvent solutions while retaining the advantages of tissue absorption.

EXAMPLE 9

Glycolide and Ethylene Carbonate

A mixture of 85 parts glycolide, 15 parts of ethylene carbonate, 0.01 parts of antimony trifluoride and 0.03 parts of triphenyphosphite were introduced into a glass tube, the tube evacuated and sealed. The sealed tube was heated at 185° for 6 hours and then cooled. The glass tube was broken to release the product, a copolymer which melted at 215°C. and which when melt spun was absorbed in mammalian tissue in between 60 and 75 days. By comparison, polyglycolic acid melts at about 225°C. Such a polymer as here produced is fabricateable at a lower spinning temperature, and because a copolymer, is more rubbery than a homopolymer. Such rubbery characteristics are advantageous in a suture in that when a knot is tied in a suture, the knot strength is a greater proportion of the straight pull strength than with the more highly oriented homopolymers.

In general, the degree of crystallinity is reduced as a comonomer is introduced into the composition. This has an advantage of greater flexibility in the fibers and better relative knot strength.

EXAMPLE 10

Coating Sutures

Homopolymeric polyglycolic acid is insoluble in the common organic solvents, as is a glycolic/lactic composition containing up to about 15 percent lactic acid units. A 50:50 mole percent copolymer of lactic and glycolic acid is soluble in xylene or toluene, both of which have been used in suture manufacture previously. A solution of the 50:50 mole percent copolymer is formed in xylene, the polyglycolic acid braid is wound on a frame, the suture braid on the frame is dipped into the solution, and on drying, the polyglycolic acid suture is stiffened, cut loose from any accumulation on the ends of the frame, and is thus coated which minimizes capillarity and improves rundown. The procedure not only reduces capillarity, but increases the stiffness, if it is surgically desirable for a particular procedure.

Multiple dipping is used to apply a thicker coat, if desired, but usually the concentration of the solution of the copolymer is adjusted to give a desired degree of stiffness to a particular suture. With bigger sutures, more stiffening may be desirable than with very small sutures, and depending on the surgical procedure and the preferences of the individual surgeon, considerable variation in stiffness may be desired, and is readily obtained.

The polyfilamentary suture is preferably kept under tension while drying so that any tendency to swell is minimized, and the diameter is kept at a minimum. A tension of the order of 50 percent of the breaking stength of the suture gives excellent results.

Alternatively, the polyfilamentary suture can be dipped in tanks in an endless system, where the suture under processing tension passes into a dip tank, and then through drying tunnels so the suture is under tension constantly, and the dipped and dried suture is wound on a takeup reel. Such a continuous system may be preferred for large scale production.

Two or more dips may be used to give a thicker coating.

For dip coating, because of the smoother surface, and because the coating prevents unraveling, it is convenient to use a twisted strand. Many polyfilamentary sutures are braided. Braiding is a comparatively expensive processing step. Twisting as in conventional thread for textile uses is a big savings in time, and permits faster processing. The present coating processes permit advantage to be taken of such methods of cost reduction.

Because a copolymer of glycolic acid/lactic acid has a lower melting point than homopolymeric glycolic acid, an extrusion process can be used to extrude a sheath over a polyfilamentary core, either braided or twisted. Extruders and techniques standard in coating wire with insulation permit rapid and economical coating. Some such systems are disclosed for other polymers in such patents as U.S. Pat. No. 2,401,291, supra, which shows a nylon on nylon coating.

U.S. Pat. Nos. 2,735,258, Crandall, and 2,824,485, Gregory, show nylon on nylon coating systems which are adaptable to the present glycolic/lactic copolymer coating on a polyglycolic acid strand, using the solvents disclosed above.

The mechanical strength is less for the copolymers than for the pure homopolymeric polyglycolic acid, but so is the brittleness. For a polymer in which flexibility is important the same 15 to 85 percent glycolic acid by weight range gives good increases in resilience, flexibility and handleability, particularly in massive sections and permits construction of bone splice pins, splice plates for broken bones and the implantation prosthetic devices in which prolonged physical strength is desirable. If a portion of copolymer of glycolic and lactic acids used as a splice plate for the bone is towards the upper range of lactic acid, absorption is so delayed that the natural bone structure has a better chance to regenerate before the absorption of the polymer occurs.

The variations in the characteristics permit adaptation to a wide variety of surgical procedures.

We claim:

1. A surgical element comprising at least one strand of polyglycolic acid insoluble in each of xylene, toluene and chloroform having thereon a stiffening and capillarity reducing quantity of a copolymer of 15 to 85 mole percent glycolic acid and 85 to 15 mole percent lactic acid, said copolymer being soluble in each of xylene, toluene and chloroform, and having a melting point sufficiently below the melting point of polyglycolic acid to permit extrusion coating without melting of the polyglycolic acid.

2. The surgical element of claim 1 wherein said element is a polyglycolic acid suture having thereon a thin but stiffening and capillarity reducing quantity of a copolymer of 15 to 85 mole percent glycolic acid and 85 to 15 mole percent lactic acid.

3. The suture of claim 2 in which the suture consists of a plurality of filaments of polyglycolic acid twisted into a strand, and coated with a twist retaining coating of said copolymer.

4. A method of retaining living mammalian tissue in a desired location and relationship during a healing process which comprises positioning and impacting said living tissue with a surgical element comprising at least one strand of polyglycolic acid insoluble in each of xylene, toluene and chloroform having thereon a stiffening and capillarity reducing quantity of a copolymer of 15 to 85 mole percent glycolic acid and 85 to 15 mole percent lactic acid, said copolymer being soluble in each of xylene, toluene and chloroform, and having a melting point sufficiently below the melting point of polyglycolic acid to permit extrusion coating without melting of the polyglycolic acid.

* * * * *